United States Patent [19]

Buysch et al.

[11] Patent Number: 5,763,717
[45] Date of Patent: Jun. 9, 1998

[54] PROCESS FOR PREPARING HYDROXYBIPHENYL

[75] Inventors: Hans-Josef Buysch, Krefeld; Christine Mendoza-Frohn, Erkrath; Jürgen Scharschmidt, Krefeld; Ulrich Notheis; Rudolf Jürgen Klee, both of Dormagen; Gerhard Darsow, Krefeld, all of Germany

[73] Assignee: Bayer Aktiengesellschaft, Leverkusen, Germany

[21] Appl. No.: 524,554

[22] Filed: Sep. 7, 1995

[30] Foreign Application Priority Data

Sep. 16, 1994 [DE] Germany .............. 44 32 977.6

[51] Int. Cl.$^6$ ............... C07C 37/06; B01J 27/25; B01J 23/26; B01J 23/24
[52] U.S. Cl. ............... 585/360; 502/201; 502/305; 502/324
[58] Field of Search ............... 502/201, 216, 502/219, 218, 305, 324; 585/360; 568/747

[56] References Cited

U.S. PATENT DOCUMENTS 4,729,977  3/1988  Immel et al. .............. 502/170
5,248,840  9/1993  Immel et al. .............. 568/747

FOREIGN PATENT DOCUMENTS 0208933  1/1987  European Pat. Off. ......... B01J 23/68

*Primary Examiner*—Glenn Caldarola
*Assistant Examiner*—Alexander G. Ghyka
*Attorney, Agent, or Firm*—Sprung Kramer Schaefer & Briscoe

[57] ABSTRACT

A description is given of the preparation of hydroxybiphenyl by dehydrogenation of completely or partially hydrogenated precursors using a supported Rh catalyst which additionally contains chromium, manganese and alkali metal and can contain a sulphur compound. The Rh catalyst which can be used according to the invention is prepared from halide-free starting materials. The Rh catalyst is distinguished by a low dependence of the initial selectivity, with the selectivity in the run-in state and the running-in time on the conditions of the reductive pretreatment and requires only short running-in times to reach the optimum state.

1 Claim, No Drawings

PROCESS FOR PREPARING HYDROXYBIPHENYL

BACKGROUND OF THE INVENTION

1. Field of the Invention

The invention relates to the preparation of hydroxybiphenyl using Rh catalysts from halogen-free salts.

2. Description of the Related Art

Supported Rh catalysts for preparing hydroxybiphenyl are known, for example, from EP 208 933.

EP 208 933 describes a supported catalyst containing from 0.1 to 5% by weight of rhodium, from 0.05 to 8% by weight of chromium and manganese together, from 0.05 to 15% by weight of alkali metal and optionally from 0.05 to 3% by weight of sulphur, based on the support material. EP 208 933 further provides for the use of these Rh catalysts for preparing hydroxybiphenyl by catalytic dehydrogenation of compounds and/or mixtures of compounds comprising completely and/or partially hydrogenated hydroxybiphenyl. The Rh catalyst described in EP 208 933 is prepared by, after heat treatment of the catalyst support treated with chromium and manganese, applying the rhodium by known methods.

A description is given of the deposition of the rhodium from an aqueous rhodium salt solution, with salt such as rhodium chloride, rhodium nitrate, rhodium acetate being mentioned without any differentiation or preference being indicated. However, the examples in EP 208 933 are based only on the use of rhodium chloride.

The Rh salt is deposited by precipitation using basic ammonium or alkali metal compounds in aqueous solution, these basic compounds being applied either before or after the Rh solution.

Regardless of the treatment with sulphur compounds which may optionally be carried out in a further preparation step, no washing procedure is finally carried out prior to drying, reductive pretreatment and the use of the catalyst for the dehydrogenation. The anion of the Rh salt, namely the chloride, remains in the catalyst.

The preparation, for example, of 2-hydroxybiphenyl over the Rh catalysts from rhodium chloride described in the examples of EP 208 933 results in the formation of a series of byproducts, including biphenylene oxide, biphenyl, phenylcyclohexane, cyclohexanone, cyclohexanol, phenol and benzene. The intermediates in the dehydrogenation to give hydroxybiphenyl, namely o-cyclohexylphenol, phenylcyclohexan-2-one and phenylcyclohexan-2-ol, are additionally obtained.

The amounts of the byproducts and intermediates formed depend greatly, according to our own studies, on the pretreatment conditions of the catalyst (reduction temperature and time). EP 208 933 describes the wide range from 120° to 450° C. for the reduction temperature and from 30 to 80 hours for the time.

Furthermore, the composition of the dehydrogenation product stream changes greatly during the running-in of the catalyst; although the selectivity for the desired product 2-hydroxybiphenyl increases during this time, a considerable amount of byproducts which can mostly no longer be used in the process is obtained, depending on the initial selectivity and depending on the required duration of the running-in phase. Long running-up phases with gradually changing product composition likewise have an adverse effect on the work-up of the dehydrogenation stream. Furthermore, the strong dependence of the dehydrogenation product composition on the time and temperature of the hydrogenative pretreatment of the catalyst places high demands on the exact adherence to these conditions.

It was therefore desirable to find an Rh catalyst for the dehydrogenative preparation of hydroxybiphenyl which avoids the difficulties described: desirable aspects are low sensitivity of the product composition on the manner of the reductive pretreatment of the catalyst, a high initial selectivity and a short running-in phase of the catalyst into its steady state of maximum selectivity.

SUMMARY OF THE INVENTION

It has now surprisingly been found that in the preparation of hydroxybiphenyl over an Rh catalyst optionally containing chromium and manganese, alkali metal and/or sulphur and on which the rhodium and optionally the further elements are deposited from halogen-free starting materials, a significant shortening of the running-in phase of the Rh catalyst is obtained. In other words, the invention relates to the fact that the anions of the catalyst active substances described as equally useful in EP 208 933 are in no way equally useful and that the consistent omission of the halide ions gives unforeseeable advantages.

The invention provides a process for preparing hydroxybiphenyl by catalytic dehydrogenation of compounds or mixtures of compounds which comprise completely or partially hydrogenated hydroxybiphenyl at 300°–400° C. and 50–1500 mbar using a supported Rh catalyst containing from 0.1 to 5% by weight of Rh, 0.05 to 8% by weight of Cr and Mn, where the weight ratio Cr:Mn=5:1 to 1:5, and from 0.05 to 15% by weight of alkali metal, all figures calculated as metal and based on the total weight of the catalyst, where the catalyst can additionally contain from 0.05 to 3% by weight of sulphur, calculated as elemental sulphur and based on the total weight of the catalyst, which is characterized in that the supports used for preparing the catalyst and the compounds of Rh, Cr. Mn, the alkali metals and S used are halogen-free.

DETAILED DESCRIPTION OF THE INVENTION

Suitable starting materials for the process of the invention for preparing hydroxybiphenyl are, for example: 2-cyclohexylidenecyclohexanone, 2-cyclohexenylcyclohexanone, 2-cyclohexylcyclohexanone, 2-cyclohexylcyclohexanol, 2-cyclohexylphenol, 3-cyclohexylphenol, 4-cyclohexyl phenol, 2-phenolcyclohexanone and 2-phenylcyclohexanol.

The compounds mentioned are readily available. Thus, for example, 2-cyclohexylidenecyclohexanone and 2-cyclohexenylcyclohexanone are obtained by condensation of cyclohexanone in the presence of acid or basic catalysts by known methods. These two compounds are also obtained, along with 2-cyclohexylcyclohexanone, 2-cyclohexylcyclohexanol, etc., as byproducts in the catalytic dehydrogenation of cyclohexanol. They can easily be separated from the dehydrogenation mixture by distillation and can be used as a mixture for the preparation of 2-hydroxybiphenyl. Cyclohexylphenol is obtained by known methods by catalytic alkylation of phenol; 2-cyclohexylphenol also occurs, along with 2-phenylcyclohexanone and 2-phenylcyclohexanol, 2-cyclohexylcyclohexanone, as byproduct in the synthesis of 2-hydroxybiphenyl. Mixtures of starting materials containing 2-cyclohexenylcyclohexanone and 2-cyclohexylidenecyclohexanone necyclohexanone in a ratio of 80–90:20–10% by weight are often available.

The catalytic dehydrogenation of the abovementioned compounds or compounds or mixtures of compounds is generally carried out by passing the compound or mixtures of compounds in vapour form over the catalyst at temperatures of from 300° to 400° C., in particular from 320° to 390° C., under atmospheric pressure or reduced pressure, for example at 50–1500 mbar.

The usual catalyst supports are suitable for preparing the Rh catalyst to be used according to the invention; in particular α- and γ-aluminium oxide, aluminium spinels, silica gel, kieselguhr, montmorillonites, pumice and/or activated carbon.

The supported catalyst to be used according to the invention has an Rh content of from 0.1 to 5% by weight, preferably from 0.2 to 2% by weight.

The rhodium is applied by known methods, e.g. by impregnation of the catalyst support in a rhodium salt solution. According to the invention, suitable rhodium salts are halogen-free Rh salts such as rhodium nitrate, acetate, sulphate, oxalate, $H_3[Rh(SO_4)_3]$, preferably rhodium nitrate. After impregnation of the catalyst, the rhodium nitrate is preferably decomposed in air and/or in a stream of nitrogen for from 2 to 48 hours at from 200° to 500° C. The Rh salt can be deposited on the support in a known manner by precipitation with alkali solution. It is here possible in principle to impregnate the support with alkali solution first, to dry it and then to apply the Rh salt solution or, the other way round, to carry out the Rh impregnation first, to dry and then further treat with alkali solution.

Suitable solutions for the alkali treatment are, for example, aqueous solutions of inorganic and/or organic alkali compounds such as the oxides, hydroxides and/or alkoxides of the alkali metals and also the salts of those weak acids which neither themselves nor in the form of their reaction products count as hydrogenation catalyst poisons in the context of the customary formulation (e.g. according to Zymalkowski: "Katalytische Hydrierung", (1965), page 36; Houben-Weyl (1955), volume 4/2, page 257), thus particularly those which are free of N, P, As, Sb, Se, Te, Cl, Br and I, such as the carbonates, bicarbonates, acetate and/or the salts of other lower carboxylic acids. Examples of alkali compounds which may be mentioned are: lithium hydroxide, sodium hydroxide, sodium carbonate, sodium hydrogen carbonate, sodium methoxide, sodium ethoxide, sodium acetate, potassium hydroxide, potassium carbonate, potassium methoxide and/or rubidium hydroxide. The concentration of the alkali compounds in the alkali solution used is generally from about 0.02 to 5N, preferably from 0.02 to 2N, in particular from 0.05 to 1N.

In a manner known from EP 208 933, sulphur compounds can additionally be applied to the catalyst. Examples of suitable sulphur compounds which may be mentioned are: the sulphates, sulphites, thiosulphates and thiocyanates of the alkali metal, preferably $K_2SO_4$, $Na_2SO_4$, $Na_2SO_3$, $Na_2S_2O_3$, KSCN and NaSCN. These salts can be used either individually or in admixture with one another. However, they can also be dissolved in water together with the alkali compounds and thus be applied in admixture to the supported catalyst. To apply the sulphur-containing compounds to the catalyst, the salts mentioned are dissolved in water and the catalyst already containing the rhodium is impregnated or sprayed with this solution.

The sulphur compounds mentioned are applied to the supported catalyst in such an amount that the latter has a sulphur content of from about 0.05 to 3% by weight, preferably from 0.1 to 1.6% by weight, based on the catalyst weight.

The catalyst to be used according to the invention can thus contain from 0.05 to 15% by weight of alkali metal, preferably from 0.1 to 10% by weight, from the alkali treatment and/or from the sulphur compound.

If, in place of the untreated support materials, supports treated with chromium and manganese in a manner known from EP 208 933 are used for preparing the catalyst of the invention, the Rh catalyst can additionally contain from 0.05 to 8% by weight, preferably from 0.2 to 5% by weight, of chromium and manganese together, based on the catalyst weight. The weight ratio of the elements chromium and manganese in the supported catalyst of the invention is from about 5:1 to 1:5, preferably from 10:9 to 1:2.

The chromium and manganese can be applied to the catalyst support, for example, by joint precipitation of a manganese-chromium hydroxide mixture from a chromium and manganese salt solution using alkali solution or ammonia and subsequent washing-out of the soluble components with water. Suitable chromium and manganese salts are likewise halogen-free salts, in particular the sulphates, acetates and/or nitrates of the said elements. The chromium and manganese can also be deposited on the catalyst support as ammonium manganese chromate or ammonium alkali metal manganese chromate from a solution of manganese(II) salts and ammonium dichromate by means of ammonia and/or basic alkali compounds. Particularly uniform and strongly adherent deposits are obtained if the addition of base is carried out slowly and uniformly while avoiding relatively large concentration differences. In a preferred embodiment, the precipitation is therefore carried out by means of urea under hydrolysing conditions, whereby the above-mentioned conditions are ensured particularly well.

After the application of the chromium and manganese compounds to the catalyst support, the catalyst support thus treated is, for example, washed free of sulphate, before it is heated to relatively high temperatures (from about 200° to 450° C., preferably from 250° to 350° C.). The catalyst support treated with chromium and manganese compounds is heat-treated for from about 0.5 to 3 hours, preferably from 1 to 2 hours.

After the last preparative step, this catalyst can be used directly for a dehydrogenation reaction, but it is more advantageous to treat it prior to use with hydrogen at from 200° to 450° C. for from 4 to 80 hours. The hydrogen is preferably diluted with inert gas. The reductive pretreatment is preferably carried out in the reactor in which the preparation of the hydroxybiphenyl also takes place.

The hydroxybiphenyl prepared by the process of the invention is used, for example, as preservative for citrus fruits or as carrier for the dyeing of dispersion dyes (cf. DE-C 20 49 809).

Examples of the catalyst preparation

Comparative example for the catalyst preparation

As described in EP 208 933 (Examples 1a and 5), 100 g of spherical γ-$Al_2O_3$ (diameter: from 2 to 5 mm) having a specific surface area of 350 $m^2$/g were initially charged in a round-bottomed flask and admixed with a solution of 3.8 g of $MnSO_4 \cdot H_2O$, 2.8 g of $(NH_4)_2Cr_2O_7$ and 22 g of urea in 72 ml of water. The flask was maintained at 85° C. for one hour while being rotated, the liquid not absorbed was filtered off, the catalyst support was washed free of sulphate and then dried for 25 hours at 110° C. under a water pump vacuum. The catalyst support thus treated was subsequently heat treated for 30 minutes at 300° C. The catalyst support thus treated with chromium and manganese was then uniformly impregnated in a round-bottomed flask with a solution of 2.03 g of rhodium trichloride in 30 ml of water. The moist catalyst pellets were dried at 100° C. The water pump vacuum and then again impregnated with a solution of 2.92 g of sodium hydroxide and 2.92 g of $K_2SO_4$ in 30 ml of water. The catalyst pellets were then dried for 43 hours at 100° C. in a water pump vacuum.

tube contained column packing which assists the vaporization of the liquid starting material prior to contact with the catalyst.

EXAMPLE 2

Samples of the catalyst from the comparative example were reduced at 250°, 325°, 375° and 425° C. respectively for 24 hours in a mixture of 10% by volume of $H_2$ and 90% by volume of $N_2$. Table I gives the results of the activity studies.

TABLE 1

| | Comparative catalyst (conversion of starting materials = 100%) | | | | |
|---|---|---|---|---|---|
| Reduction of the catalyst at T [°C.] | Initial selectivity for 2-hydroxy biphenyl | Duration of the running-in phase | Selectivity for 2-hydroxy biphenyl in the steady state | Total of recyclable intermediates in the steady state | Total of non-recyclable byproducts in the steady state |
| 250 | 44% | 200 h | 69% | 10.9% | 20.1% |
| 325 | 49% | 110 h | 71% | 9.5% | 19.5% |
| 375 | 53% | 100 h | 79% | 5.0% | 16.0% |
| 425 | 76% | 80 h | 83% | 4.8% | 12.2% |

EXAMPLE 1

The catalyst was prepared as in the comparative example. However, the catalyst support treated with chromium and manganese was impregnated with a solution of 2.8 g of $Rh(NO_3)_3$ in 30 ml of water instead of with a solution of rhodium trichloride, dried at 100° C. in a water pump vacuum and heat treated in air for 3 hours at 300° C. The further treatment with alkali and sulphur compound and the final drying were carried out as in the comparative example.

Examples of catalyst use

Prior to use of the catalysts in the preparation of hydroxybiphenyl, they were pretreated by reduction in a mixture of 10% by volume of $H_2$ and 90% by volume of $N_2$. Reduction temperature and time are in each case given in the examples.

The examples of catalyst use described comprise the preparation of 2-hydroxybiphenyl. For the activity studies, 5 ml of the rhodium-containing supported catalyst were in each case heated to the desired reaction temperature (360° C.) in a vertically arranged, electrically heatable glass tube having a length of about 70 cm and an internal diameter of 17 mm. The starting material to be dehydrogenated, a mixture of 2-cyclohexenylcyclohexanone and 2-cyclohexylidenecyclohexanone (85:15% by weight), was introduced into the reaction tube at the top at a metering rate of 1 g/h by means of a perfusion pump. The upper part of the Recyclable intermediates are: o-cyclohexylphenol and phenylcyclohexan-2-ol.

Non-recyclable byproducts are: biphenylene oxide, biphenyl, phenylcyclohexane, one, cyclohexanol, phenol, benzene.

EXAMPLE 3

Samples of the catalyst from the Example 1 were reduced at 250°, 325°, 375° and 425° C. respectively for 24 hours in a mixture of 10% by volume of $H_2$ and 90% by volume of $N_2$. For results, see Table 2.

TABLE 2

| | Selectivity for 2-hydroxybiphenyl; catalyst from Example 1 (conversion of starting materials = 100%) | | | | |
|---|---|---|---|---|---|
| Reduction of the catalyst at T [°C.] | Initial selectivity for 2-hydroxy biphenyl | Duration of the running-in phase | Selectivity for 2-hydroxy biphenyl in the steady state | Total of recyclable intermediates in the steady state | Total of non-recyclable byproducts in the steady state |
| 250 | 61% | 70 h | 74% | 19.0% | 7.0% |
| 325 | 57% | 60 h | 74% | 20.1% | 5.9% |
| 375 | 63% | 50 h | 76% | 16.7% | 7.3% |
| 425 | 71% | 30 h | 78% | 12.2% | 9.8% |

Recyclable intermediates are: o-cyclohexylphenol and phenylcyclohexan-2-ol. Non-recyclable byproducts are: biphenylene oxide, biphenyl, phenylcyclohexane, cyclohexanone, cyclohexanol, phenol, benzene.

The comparative catalyst from rhodium chloride in Example 2 shows:

a strong dependence of the initial selectivity of the pretreatment of the catalyst a strong dependence of the selectivity in the run-in state on the pretreatment of the catalyst a strong dependence of the running-in time on the pretreatment of the catalyst long running-in times.

In contrast, the catalysts prepared from halogen-free salts in Example 3 have, in comparison with Example 2, a far lower sensitivity of the initial selectivity the selectivity in the steady state and the running-in time on the manner of the reductive pretreatment. Furthermore, they require considerably shorter running-in times to reach the run-in state of optimum selectivity from their in any case good initial selectivities.

The advantage of the catalysts prepared so as to be halogen-free can be seen particularly when the percentages in the product stream of desired product 2-hydroxybiphenyl and of intermediates which can be recycled to the dehydrogenation are added. Here, the catalyst from rhodium nitrate (Example 3) is distinguished in particular by its very low proportion of non-recyclable byproducts.

What is claimed is:

1. A process for preparing hydroxybiphenyl which comprises catalytic dehydrogenation of compounds or mixtures of compounds which comprise completely or partially hydrogenated hydroxybiphenyl at 300°–400° C. and 50–1500 mbar using a supported rhodium nitrate catalyst containing from 0.1 to 5% by weight of Rh, 0.05 to 8% by weight of Cr and Mn, where the weight ratio Cr:Mn =5:1 to 1:5, and from 0.05 to 15% by weight of alkali metal, all figures calculated as metal and based on the total weight of the catalyst, where the catalyst can additionally contain from 0.05 to 3% by weight of sulphur, calculated as elemental sulphur and based on the total weight of the catalyst, wherein the support used for preparing the supported catalyst, the rhodium nitrate and the compounds of Cr, Mn, the alkali metals and S used are halogen-free and wherein the rhodium nitrate present on the catalyst support is decomposed over a period of from 2 to 48 hours at from 200° to 500° C. in the presence of air or nitrogen.

* * * * *